United States Patent [19]
Sierks et al.

[11] Patent Number: 5,162,210
[45] Date of Patent: Nov. 10, 1992

[54] PROCESS FOR ENZYMATIC HYDROLYSIS OF STARCH TO GLUCOSE

[75] Inventors: Michael Sierks, Glenview, Ill.; Birte Svensson, Vanlose, Denmark

[73] Assignee: Iowa State University Research Foundation, Ames, Iowa

[21] Appl. No.: 546,511

[22] Filed: Jun. 29, 1990

[51] Int. Cl.$^5$ .................. C12P 19/20; C12N 9/34; C12N 9/26; C12N 15/00

[52] U.S. Cl. .................. 435/96; 435/205; 435/201; 435/172.3; 435/69.1

[58] Field of Search .................. 435/96, 69.1, 172.3, 435/201, 205, 96.1–96.6

[56] References Cited

U.S. PATENT DOCUMENTS 4,560,651 12/1985 Nielsen et al. .................. 435/25

OTHER PUBLICATIONS

Svensson, B., et al., 1983, Carlsberg Research Communications 48:529–544.
Svensson, B., et al., 1986, European Journal of Biochemistry 154:497–502.
Hakansson, K., et al., 1989, Carlsberg Research Communications 54:145–156.
Svensson, B., et al., 1990, European Journal of Biochemistry 188:29–38.
Meagher, M. M., et al., 1989, Biotechnology and Bioengineering, vol. 34, No. 5:689–693.
Leatherbarrow, R. J., et al., 1986, Protein Engineering, vol. 1, No. 1: 7–16.
Harada, T., 1984, Biotechnology and Genetic Engineering Reviews, vol. 1: 39–63.
Tanaka, Y. et al., (1986) Comparison of amino acid sequence of three glucoamylases and their structure function relationships, Agric. Biol. Chem., 50, 965–969.
Itoh T., et al., (1987) Nucleotide sequence of the glucoamylase gene GLU1 in yeast Saccaromycopsis fibuligera. J. Bacteriol., 169, 4171–4176.
Hiromi, K., (1970) Interpretation of dependency of rate parameters on the degree of polymerization of substrate in enzyme-catalyzed reactions, Evaluation of subsite affinities of exo-enzyme, biochem. Biophys. Res. Commun., 40, 1–6.
Savek'ev, A. N. et al., (1982) Carboxyl groups in active site of glucoamylase from Aspergillus awamori, Biochemistry (USSR), 47, 1365–1367.
Tanaka, A. et al., (1983) Fractionation of Isozymes and determination of the subsite structure of glucoamylase form Rhizopus niveus. Agr. Biol. Chem., 47, 573–580.
Koyama, T., et al., (1984) subsite affinity of the glucoamylase from Aspergillus saitoi. Chem. Pharm. Bull., 32, 757–761.
Meagher, M. M., (1989) Subsite mapping of Aspergillus niger Glucoamylases I and II with malto-and isomaltooligosaccharides, Biotechnol. Bioeng., 34, 681–688.
Svensson, B. (1988) Regional distant sequence homology between amylases, a-glucosidases and transglucanosylases, FEBS Lett., 230, 72–76.
Nikolov, Z. L., et al., (1989) Kinetics, equilibria and modeling of the formation of oligosaccharides from D-glucose with Aspergillus niger glucoamylases I and II, Biotechnol. Bioeng., 34, 694–704.

(List continued on next page.)

Primary Examiner—Robert A. Wax
Assistant Examiner—William W. Moore
Attorney, Agent, or Firm—Tilton, Fallon, Lungmus & Chestnut

[57] ABSTRACT

A process for converting starch or partially hydrolyzed starch into a syrup containing dextrose includes the steps of saccharifying starch hydrolyzate in the presence of a saccharifying starch hydrolyzate in the presence of a mutated glucoamylase or related enzyme and increasing the selectivity of the enzyme for α-(1→4)-glucosidic bonds by the glucoamylase or related enzyme by including at least one mutation, the mutation substituting an amino acid of the enzyme with at least one amino acid chosen by comparison with structurally related regions of other enzymes that selectively hydrolyze only α-(1→4) glucosidic bonds.

Enzymes made in accordance with the present invention are also disclosed.

12 Claims, 4 Drawing Sheets

OTHER PUBLICATIONS

Sierks, M. R. et al., (1989) Site-directed mutagenesis at the active site Trp120 of *Aspergillus awamori* glucoamylase, *Protein Eng.*, 2, 621–625.

Sierks, M. R., et al.,(1990) Catalytic Mechanism of fungal (Glucoamylase as defined by mutagenesis of Asp176, Glu179 and Glu180 in the enzyme from *Asperigillus awamori*, *Protein Eng.*, 3, 193–198.

Pazur, J. H. et al., (1967) Properties of the glucoamylase from Rhizopus delemar, *Carbohydr. Res.*, 4, 371–379.

Watanabe, T. et al., (1969) Reversion product from D-glucose by purified Phizopus niveus glucoamylase, *Starke*, 21, 18–21.

Watanabe, T. et al., (1969) Reversion product from D-glucose by purified Endomyces sp. glucoamylase. *Starke*, 21, 44–47.

Hehre, E. J. et al., (1969) Configurational specificity unappreciated key to understanding enzymic revrsions and de novo glucosidic bond synthesis. *Arch. Biochem. Biophys.*, 135, 75–89.

Pazur, J. H. et al., (1977) Comparison of the action of glucoamylase and glucoslytransferase on D-glucose, maltose, and malto–oligosaccharides. *Carbohydr. Res.*, 58, 193–202.

Pazur, J. H. et al., (1959) The action of an amyloglucosidase of Aspergillus niger on starch and maltooligodextrins. *J. Biol. Chem.*, 234, 1966–1970.

Clarke, A. J. & Svensson, B. (1984) Identification of an essential tryptophonyul residue in the primary structure of glucoamylase G2 from Aspergillus niger. *Carlsberg Res. Comman.*, 49, 559–566.

Innis, M. A. et al., (1985) Expression, Glycoslyation, and secretion of an *Aspergillus* glucoamylase by *Saccaromyces cerevisiae, Science*, 228, 21–26.

Sierkes, M. R., (1988) Ph. D. Thesis, Iowa State University.

Bock, K & Sigursshojold, B. W. (1989) Mechanism and binding specificity of B-glucosidase catalyzed nydrolysis of cellobiase analogues studied by competition enzyme kinetics monitored by HNMR spectroscopy *Eur. J. Biochem.*, 178, 711–720.

Fig-1 a) Region 1

Glucoamylases:
- An -109 FNVDETAYTGSWGR
- Ro -268 FNPDGSGYTGAWGR
- Sd -455 WNVDNTAFTEDWGR
- Sf -155 FNTDGSAYTGAWGR α-Amylase:
- Ao -072 DCAYGDAYTGYWQT Cyclodextrin glucanotransferases:
- aB -090 SGVNNTAYHGYWAR
- Kp -083 DAAGNTGYHGYWGR b) Region 4

α-1,4-/α-1,6-Hydrolases (Glucoamylases):
- An -174 GYD-LWEEVNGS
- Ro -309 CFD-LWEEVNGV
- Sd -527 GFD-LWEEVNGM
- Sf -232 GFD-LWEENQGR α-1,6-Hydrolase (Isomaltase):
- Rl -498 NYDGLWIDMNEV α-1,4-Hydrolases:
- α-Amylases
  - Fungal: Ao -199 SIDGLRIDTVKH
  - Mammalian: Pp -190 GVAGFRLDASKH
  - Bacterial: Bs -169 GADGFRFDAAKH
  - Cereal: Ba -173 GFDAWRLDFARG
- Maltase: Sc -207 GVDGFRIDTAGL
- Cyclodextrin Glucanotransferases:
  - aB -222 GVDGIRFDAVKQ
  - Kp -216 GVDAIRIDAIKH c) Region 6

| | | | | | | | | | | | | | |
|---|---|---|---|---|---|---|---|---|---|---|---|---|---|
| Bacterial α-amylase | Bs | 318- | E | W | A | V | T | F | V | E | N | H | D | T | Q | P | G | Q | S |
| Cereal α-amylase | Ba | 281- | A | K | K | A | A | T | F | V | D | N | H | D | T | G | S | T | Q | A |
| Mammalian α-amylase | Pp | 290- | D | R | A | L | V | F | V | D | N | H | D | N | Q | R | G | H | G |
| Fungal a/α-amylase | Ao | 287- | T | I | L | G | T | F | V | E | N | H | D | N | P | R | F | A | S | I |
| Maltase | Sc | 339- | S | W | A | T | Y | Y | I | V | E | T | H | A | Q | S | N | S | M |
| A. niger glucoamylase | An | 382- | D | G | F | V | S | I | V | E | T | H | D | M | D | R | F | Q | V |
| B. Macerans CGTase | Bm | 319- | N | N | M | V | T | F | I | D | N | H | D | M | D | R | F | Q | V |

```
          SalI                        gct                             NotI
          GTC GAC GAG ACT GCC         TAC ACT GGT         tac         TGG GGG CGG CCG CAG...
                                                         TCT
          Val Asp Glu Thr Ala         Tyr Thr Gly         Ser         Trp Gly Arg Pro Gln
          Val                         Tyr                 Ser                           124
          111                         116                 119

SnabI                                                 a    c               c
          ...TAC GTA GCT CAA TAC TGG AAC CAG ACA GGA TAT GAT CTC TGG GAA GAA...
          Tyr Val Ala Gln Tyr Trp Asn Gln Thr Gly Tyr Asp Leu Trp Glu Glu
          165                                                 177 178
                                                                              ApaI
          HpaI  gct aag cac
          ...GTT ACC GGC TCG TCT TTC TTT ACG ATT GCT GTG CAA CAC CGG GCC CTT...
          Val Asn Gly Ser Ser Phe Phe Thr Ile Ala Val Gln His Arg Ala Leu
          182 183 184                                                     196
```

PROCESS FOR ENZYMATIC HYDROLYSIS OF STARCH TO GLUCOSE

TECHNICAL FIELD

The present invention relates to novel enzymes and a method of utilizing the enzymes for producing glucose from starch. More specifically, the present invention relates to the use of mutated glucoamylase enzymes for increasing the yield of glucose produced from a unit of starch or partially hydrolyzed starch.

BACKGROUND ART

Glucoamylase (1,4-α-D-glucan glucohydrolase, EC 3.2.1.3) is an enzyme which catalyzes the release of D-glucose from the nonreducing ends of starch or related oligo- and polysaccharide molecules. Glucoamylases are produced by several filamentous fungi and yeasts, with those from Aspergilli being commercially most important.

Commercially, the glucoamylase enzyme is used to convert cornstarch which is already partially hydrolyzed by α-amylase to glucose. The glucose is further converted by glucose isomerase to a mixture composed almost equally of glucose and fructose. This mixture, or the mixture further enriched with fructose, is the commonly used high fructose corn syrup commercialized throughout the world. This syrup is the world's largest tonnage product produced by an enzymatic process. The three enzymes involved in the conversion of starch to fructose are among the most important industrial enzymes produced, even though two of them, α-amylase and glucoamylase, are relatively inexpensive on a weight or activity basis.

Two main problems exist with regard to the commercial use of glucoamylase in the production of high fructose corn syrup. The first problem is with regard to the thermal stability of glucoamylase. Glucoamylase is not as thermally stable as α-amylase or glucose isomerase and it is most active and stable at lower pH's than either α-amylase or glucose isomerase. Accordingly, it must be used in a separate vessel at a lower temperature and pH. Second, at the high solids concentrations used commercially for high fructose corn syrup production, glucoamylase synthesizes di-,tri-, and tetrasaccharides from the glucose that is produced. Accordingly, the glucose yield does not exceed 95% of theoretical. By quantity, the chief by-product formed is isomaltose, a disaccharide containing two glucosyl residues linked by an α-(1→6) bond. A glucoamylase that can produce glucose without by-products would be of great commercial potential if its cost were not significantly higher than that of the current enzyme being produced, which is made by the two very closely related fungal species *Aspergillus niger* and *Aspergillus awamori*. The glucoamylases from these two sources are identical.

Glucoamylases from a variety of fungal sources have been sequenced and have high homology (1,2). The high homology between the variety of fungal sources suggests that the enzymes are all structurally and functionally similar. Furthermore, kinetic measurements on a number of glucoamylases have demonstrated that their subsite binding energies are almost identical (3,4,5,6,7).

Applicant has conducted studies of the homology of amino acids from identical *A. niger* and *A. awamori* glucoamylases, both with other glucoamylases and with other enzymes that hydrolyze starch and related substances (8). This was done to identify amino acids that were common to enzymes that cannot cleave α-(1→6) glucosidic bonds (chiefly α-amylases) from those that can hydrolyze α-(1→6) glucosidic bonds (glucoamylases and isomaltase).

Applicant has found that glucoamylase is represented in three out of six regions of sequence similarity among several starch hydrolases (8). It has been determined that Region 1 from *A. niger* glucoamylase residues 109–122, Region 4 from glucoamylase residues 172–184, and Region 6 from residues 382–398 contain these sequence similarities. The regions represent sequence similarities among enzymes cleaving only α-(1→4) bonds, enzymes cleaving only α-(1→6) bonds, and glucoamylase, which cleaves both. Amino acids at positions 178, 182, 183 and 184 differed between the groups, which suggested changing amino acids at these positions. Applicant has also noted homology at position 119. By utilizing cassette mutagenesis, applicant made substitutions of amino acids at these various positions consistent with the homology studies (8).

In connection with the fourteenth ICS meeting in Stockholm in 1988, applicant presented a poster disclosing that site-directed mutagenesis supports the participation of Tyr116 and Trp120 in substrate binding and Glu180 in catalysis. Moreover, a role was suggested for Trp170 in isomaltose binding, but this aspect remains to be studied by site-directed mutagenesis. The poster also disclosed that the mutation of Asn182 to Ala provided an active enzyme, but no results were disclosed or suggested regarding relative specificity of that enzyme.

Figure 1:
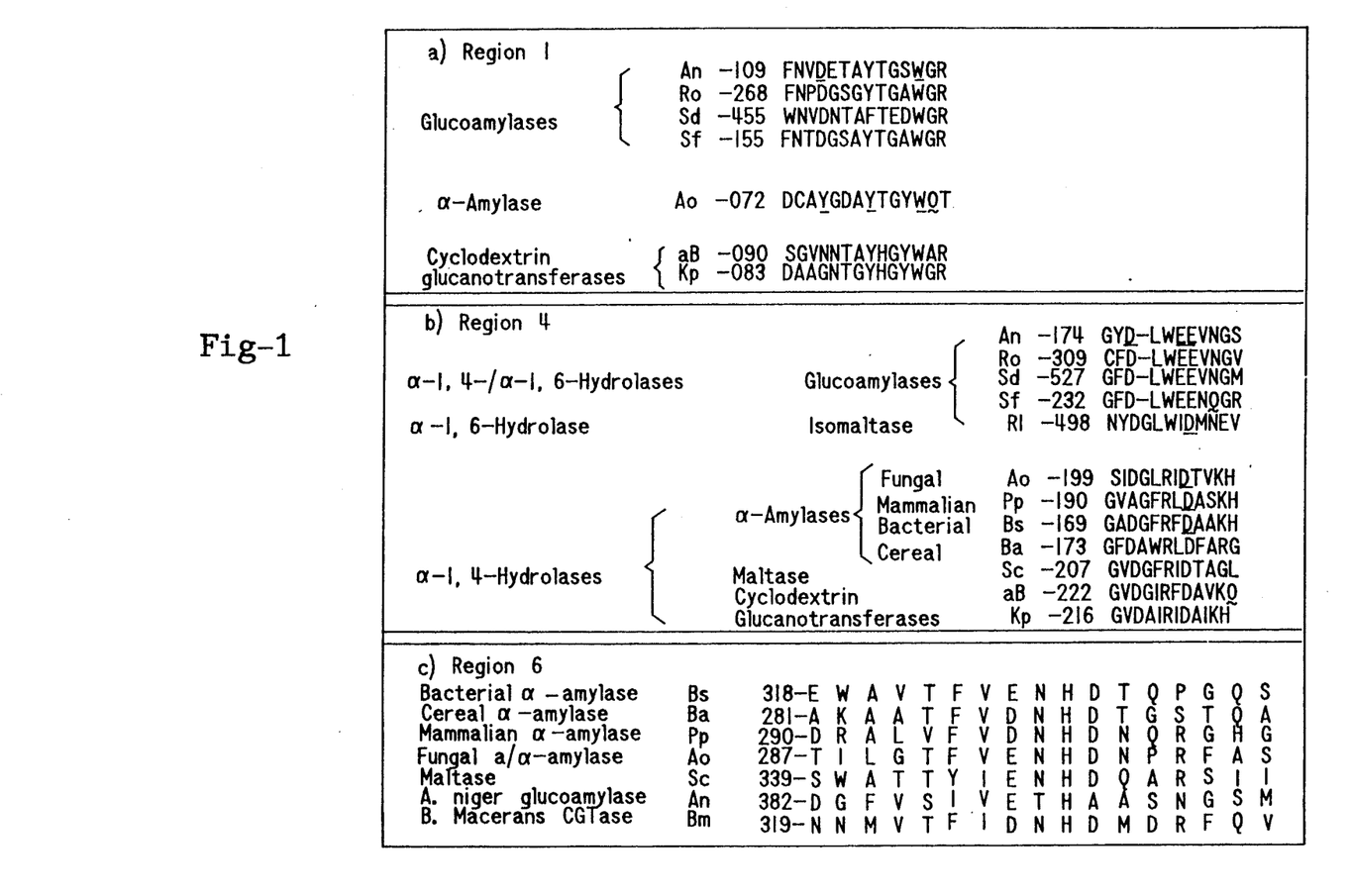

As stated above, a drawback in the industrial use of glucoamylase is that D-glucose yields are limited to approximately 95% in concentrated starch solutions. This occurs because of the slow hydrolysis of α-(1→6)-D-glucosidic bonds in starch and the formation of various accumulating condensation products, mainly α-(1→6)-linked isomaltooligosaccharides, in a stepwise manner from D-glucose (9). A reduction of the rate that glucoamylase cleaves and therefore forms α-(1→6) bonds relative to the rate it cleaves α-(1→4) bonds has practical implications. Mutations at Trp120, Asp176, Glu179 and Glu180 in *A. awamori* glucoamylase all were critical for enzyme activity (10, 11). Applicant proceeded to investigate further amino acid mutations in order to increase the selectivity of glucoamylase for maltose over isomaltose hydrolysis. These experiments are problematic since the three-dimensional structure of glucoamylase has not been determined. Instead, primary use was made of regional sequence similarities with glucoamylases other than those produced by *A. awamori* and *A. niger* as well as with other enzymes active on α-(1→4)- and α-(1→6)-linked D-glucosyl oligo- and polysaccharides (FIG. 1).

Applicant thus conducted tests, for example involving mutations of Ser119, Leu177, Trp178, Asn182, Gly183, and Ser184.

In Region 1 (FIG. 1), the glucoamylases at positions corresponding to *A. niger* 119 have either Ser, Ala or Pro where the α-amylases and cyclodextrin glucanotransferases (CGTase) all have Tyr. Therefore, Ser119 of *A. niger* glucoamylase was mutated to Tyr so it would resemble the α-amylases and CGTases.

In Region 4, Leu177 was mutated to His, since enzymes active on α-(1→6)glucosidic bonds characteristically contain amino acid residues with smaller aliphatic side chains at this homologous position, while enzymes active only at α-(1→4)-D-glucosidic bonds contain primarily Phe or Trp, which have large aromatic side chains. Ile, Val and Leu also occur at this position.

At residue 178 in *A. niger* glucoamylase Trp was mutated to Arg because Trp was conserved in the glucoamylases and isomaltase which cleave α-(1→6) bonds, but Arg is found in all of the α-amylases, maltases, CGTase, amylomaltase and branching enzyme which do not.

Asn182 was mutated to Ala based on similar comparisons because Asn was conserved in all of the glucoamylases and isomaltase but was replaced with residues containing short aliphatic side chains such as Ala, Val, and Ser, usually Ala, in most of the α amylases.

At *A. niger* glucoamylase position 183, the glucoamylases all have Gly, isomaltose has an acidic side chain Glu, while the enzymes cleaving only α-(1→4) glucosidic bonds have a basic side chain, primarily Lys, although Arg also occurs. Branching enzyme is the sole α-(1→4) acting enzyme which does not have a basic group at this position, but instead has Ala there.(8) Therefore, Gly183 was changed to Lys.

At position 184, the glucoamylases have Ser, Val and Met, while isomaltase also has Val. However, the enzymes cleaving α-(1→4) bonds contain predominantly His at this position, though Gly, Leu, Gln, and Ser also occur. Therefore, Ser184 was changed to His.

Pursuant to the present invention, all of the above changes were constructed to make glucoamylase resemble more closely the α-(1→4) bond hydrolyzing enzymes and less closely the α-(1→6) bond hydrolyzing enzymes.

The Leu177→His mutation resulted in a loss of selectivity and the Trp178→Arg mutation resulted in increased selectivity, but with substantial losses in activity, whereas applicant found increased relative selectivity of hydrolysis of α-(1→4) bonds over α-(1→6) bonds with either only a small loss of activity or none at all with mutations at the 119, 182, 183, and 184 positions. These results provide highly significant commercial potential.

SUMMARY OF THE INVENTION

In accordance with the present invention there is provided a process for converting starch into a syrup containing dextrose, the process including the steps of saccharifying starch hydrolyzate in the presence of a mutated glucoamylase or related enzyme, and increasing the selectivity of the glucoamylase or related enzyme for α-(1→4) glucosidic bonds by the glucoamylase or related enzyme including at least one mutation, the mutation substituting an amino acid of the glucoamylase or related enzyme with an amino acid chosen by comparison with functionally homologous regions of other enzymes that selectively hydrolyze only α-(1→4)-glucosidic bonds.

FIGURES IN THE DRAWINGS

Other advantages of the present invention will be readily appreciated as the same becomes better understood by reference to the following detailed description when considered in connection with the accompanying drawings wherein:

FIG. 1 shows a comparison of Region 1 (a) Region 4 (b) and Region 6 (c) of *A. niger* glucoamylase with other glucoamylases, -amylases, isomaltase, maltase and cyclodextrin glucanotransferases (8) (Glucoamylases indicated as: An:*A. niger*, Ro:*Rhizopus oryzae*, Sd:*Saccharomyces diastaticus*, and Sf:*Saccharomycopis fibuligera*; -amylases indicated as: Ao:*Aspergillus oryzae*, Pp:*porcine pancreatic*, Bs:*Bacillus subtilis*, and Ba:Barley Isozyme 1; RI:Rabbit intestinal isomaltase; maltase indicated as: Sc:*Saccharomyces cerevisiae*; Cyclodextrin glucanotransferases indicated as: aB:alkalophilic *Bacillus sp.* strain 1011 and Kp:*Klebsiella pneumoniae*; shadowed areas represent sequence comparisons at the six positions mutated in GA; underlines indicate identified functionally important residues; * indicates GA catalytic groups);

DETAILED DESCRIPTION OF THE INVENTION

The present invention provides a novel enzyme and a method of using the enzyme for producing glucose from starch. Generally, the method includes the steps of partially hydrolyzing precursor starch in the presence of α-amylase and then further hydrolyzing the release of D-glucose from the nonreducing ends of the starch or related oligo- and polysaccharide molecules in the presence of glucoamylase by cleaving α-(1→4) and α-(1→6) glucosidic bonds.

The present invention also relates to enzymes that are considered to be related to glucoamylase. For example, this group of related enzymes includes α-amylase, glucosyltransferase and α-glucosidase.

More particularly, the partial hydrolysis of the precursor starch utilizing α-amylase provides an initial breakdown of the starch molecules by hydrolyzing internal α-(1→4) linkages. In commercial applications, the initial hydrolysis using α-amylase is run at a temperature of approximately 105° C. A very high starch concentration is processed, usually 30% to 40% solids. The initial hydrolysis is usually carried out for five minutes at this elevated temperature. The partially hydrolyzed starch can then be transferred to a second tank and incubated for approximately one hour at a temperature of 85° to 90° C. to derive a dextrose equivalent (D.E.) of 10 to 15.

The step of further hydrolyzing the release of D-glucose from the nonreducing ends of the starch or related oligo- and polysaccharides molecules in the presence of glucoamylase is generally carried out in a separate tank at a reduced temperature between 30° and 60° C. Preferably the temperature of the substrate liquid is dropped to between 55° and 60° C. The pH of the solution is dropped from 6 to 6.5 to a range between 3 and 5.5. Preferably, the pH of the solution is 4 to 4.5.

The glucoamylase is added to the solution and the reaction is carried out for 48 to 72 hours.

As mentioned above, condensation products are formed including α-(1→6)-linked isomaltooligosaccharides. The kinetics of reversion are set forth in detail by Nikolov et al, 1988 (9). The significance of this reversion reaction is that although glucoamylase is capable of hydrolyzing all D-glucosidic linkages found in starch, D-glucose yields higher than 95% of theoretical are not achieved in concentrated starch dextrin solutions because of the occurrence of condensation reactions involving D-glucose, commonly referred to as reversion reactions (12-16).

The condensation reaction is a bimolecular reaction whereas the hydrolysis reaction is a unimolecular reaction. Therefore, utilizing a high solids concentration as commonly utilized in industrial applications leads to formation of significant amounts of the condensation products. Although the processing of the starch at lower concentrations would reduce the condensation products, such a change is commercially unwanted. This results from the fact that it is very expensive to either ship the unconcentrated glucose product solution (having a high weight relative to concentrated product syrup) or to boil off the liquid to concentrate the glucose product.

In accordance with the present invention, an improvement is provided by incubating the partially hydrolyzed starch or related oligo- and polysaccharide molecules in the presence of the glucoamylase or related enzymes including at least one mutation substituting an amino acid chosen by comparison with the structurally related regions of other enzymes that exclusively hydrolyze only α-(1→4)-glucosidic bonds. This rationale is used to increase the selectivity of the enzymes for α-(1→4)-glucosidic bonds. As set forth in the Background Art section, these mutations were derived from sequence comparison studies by applicant from identical A. niger and A. awamori glucoamylases. As stated above, these studies identified amino acids that were common to the related enzymes that cannot hydrolyze α-(1→6)-glucosidic bonds from those that can hydrolyze α-(1→6)-glucosidic bonds.

More specifically, the mutation of the amino acids were made at positions corresponding to A. niger in Region 1 residues 109-122, Region 4 residues 172-184, and Region 6 residues 382-398 mutated to the amino acids of homologous positions of the enzymes which selectively hydrolyze only α-(1→4)-glucosidic bonds. Specific mutations showing increased selectivity for maltose hydrolysis are made at positions 119, 182, 183, and 184. Applicant further shows a significant increase in yield of glucose per unit amount of starch hydrolyzed by the mutated glucoamylase with Ala182 compared to the relative yield by the wild type glucoamylase with Asn182.

It has been found that the mutated glucoamylase with Ala182 provides a significantly higher maltose/isomaltose selectivity (selectivity for α-(1→4) glucosidic bond hydrolysis as compared to α-(1→6) glucosidic bond hydrolysis) while having only a small decrease in activity. Moreover, isomaltose formation from 30% glucose by the mutated Asn182→Ala glucoamylase was only 20% that of wild-type glucoamylase, as measured by NMR demonstrated Asn182→Ala to reduce the initial rate by 80% compared to wild-type enzyme. After 33½ hours of incubation, the isomaltose content reached in the presence of mutant enzyme was estimated to be approximately one third of that reached in the presence of the equivalent amount of wild-type enzyme. Further, a statistically significant increase in glucose yield is produced by the mutated glucoamylase Asn182→Ala compared to wild-type glucoamylase. Applicant has found an approximately 1% increase in glucose yield (1% of the remaining 5% of potential gain in yield; i.e. from 95% to 96%). Applicant has created an enzyme increasing glucose yield by at least 20% of the remaining available yield. This is accomplished by the glucoamylase mutation having increased specificity for hydrolyzing α-(1→4)-glucosidic bonds preferentially over α-(1→6)-glucosidic bonds while maintaining at least 75% of the activity of the enzyme, based on hydrolysis of the disaccharide maltose.

The mutated glucoamylase can be used in the present inventive process in combination with an enzyme that hydrolyzes only α-(1→6) glucosidic bonds in molecules with at least four glucosyl residues. Preferentially, the mutated glucoamylase can be used in combination with pullulanase or isoamylase. The use of isoamylase and pullulanase for debranching, the molecular properties of the enzymes, and the potential use of the enzymes with glucoamylase is set forth in G. M. A. van Beynum et al, *Starch Conversion Technology*, Marcel Dekker, New York, 1985, 101-142.

FIG. 1 shows a comparison of the Regions 1, 4, and 6 of A. niger glucoamylase having structural similarities with other glucoamylases, α-amylases, isomaltase, maltase, and CGTase. As discussed above, this chart indicates the rationale behind the substitution strategy practiced to derive the novel enzymes of the present invention.

Figure 2:
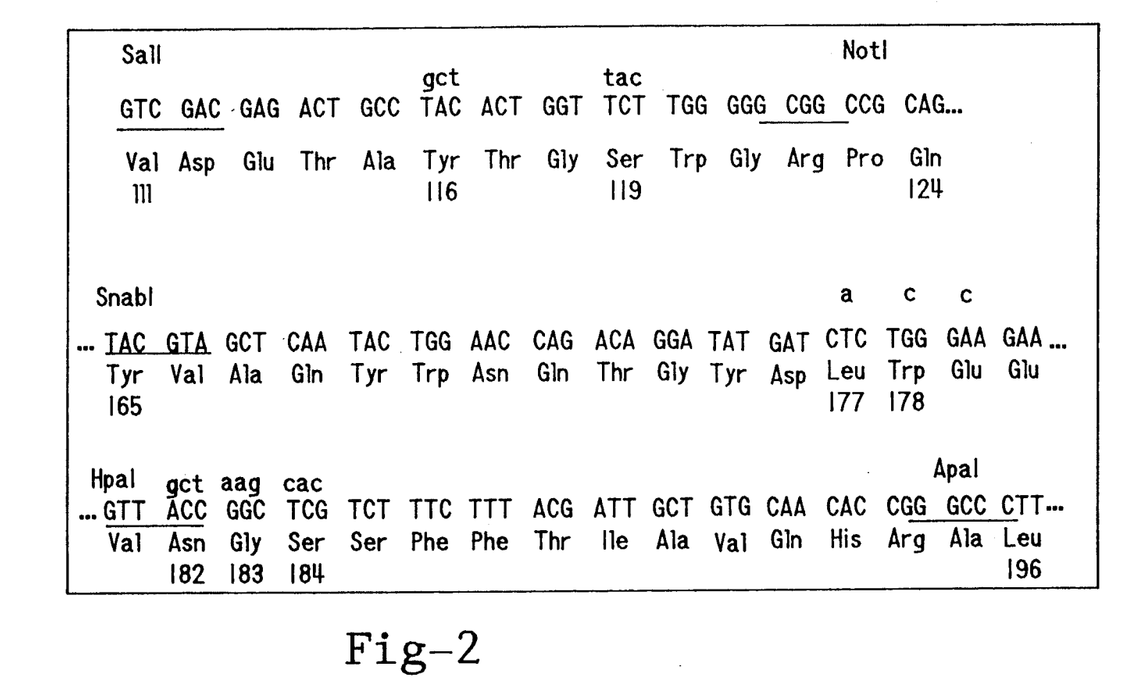
FIG. 2 is a diagram showing mutations of Ser119, Leu177, Trp178, Asn182, Gly183, and Ser184 of *A. awamori* glucoamylase, nucleotide changes being shown in small letters above the wild-type sequence.

FIG. 2 shows a diagram of the mutations of Ser119, Leu177, Trp178, Asn182, Gly183, and Ser184 of the A. awamori glucoamylase. Nucleotide changes are shown in small letters above the wild-type sequence. The mutations at positions 119, 182, 183, and 184 are the subjects of the present invention.

The preparation of the mutant genes, the source of the wild-type genes, and the isolation and cloning processes are set forth in detail by Sierks et al., 1989 (10). Enzyme reagents, and construction of mutations using cassette mutagenesis were carried out as described in the Sierks et al., 1989 reference (10). The Asn182→Ala mutation was constructed in the HpaI-ApaI cassette by using the nucleotides 5'-ATGGGCCCGGTGTTGCACATTCGTAAG-3' and 5'-GCTGGCTCGTCTTTCTTTAC-GATTGCTGT-3' as cassette and mutagenic primers, respectively, containing a 15-base-pair overlap. The following oligonucleotides were used for construction of the 119, 183 and 184 mutants.

Ser ⟶ Tyr119 CGG CCG CCC CCA GTA ACC AGT GTA G

Gly ⟶ Lys183 CGT AAA GAA AGA GCT CTT GTT AAC TTC TTC

Ser ⟶ His184 CGT AAA GAA AGA GTG GCC ATT AAC TTC TTC
CCA

Construction of the mutants were carried out as described above. Production, purification, and kinetic characterization of the mutated enzyme were performed as disclosed by Sierks et al., 1989 (10, 11).

Figure 3:
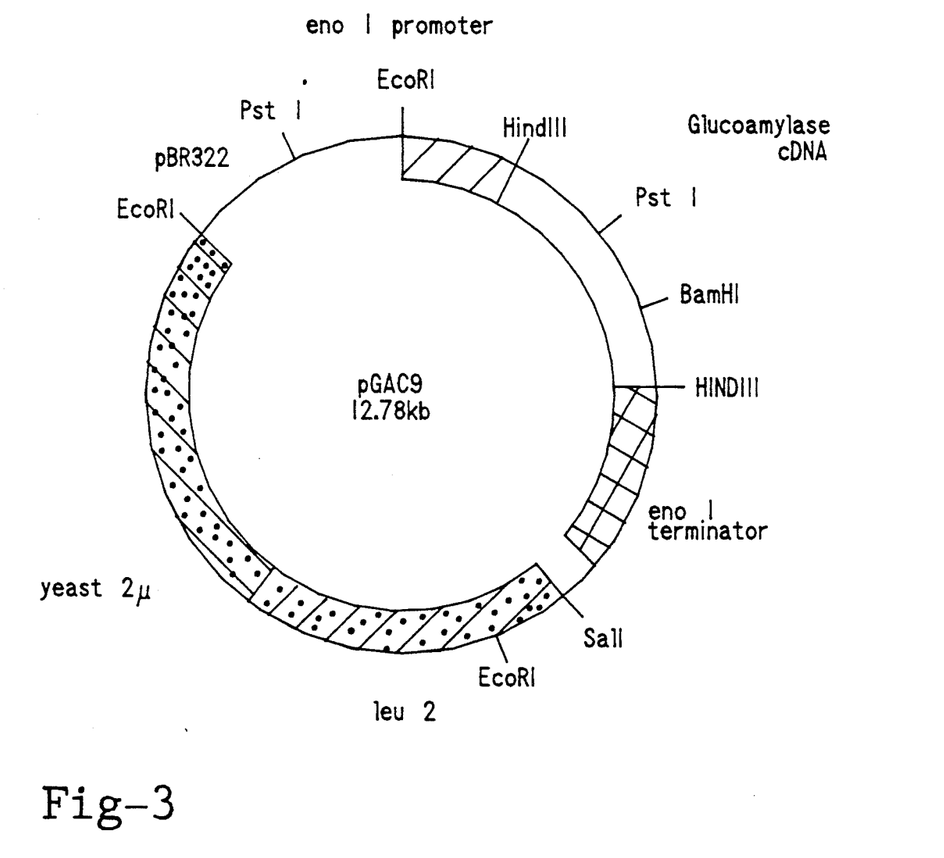
FIG. 3 show a diagram of a plasmid pGAC9 (20) with restriction sites indicated.

The identification of the plasmid and description of the procedure for introducing the gene into a plasmid are disclosed in detail in the Sierks et al., 1989 paper (10). The reference discloses plasmid purification, subcloning, and sequencing, as well as cassette mutagenesis. A diagram of the plasmid with restriction sites is shown in FIG. 3. The reference further discloses the expression of the gene and production and purification of the glucoamylase enzyme.

FIG. 3 specifically shows plasmid pGAC9. The plasmid containing the glucoamylase gene in a yeast strain, S. cerevisiae C468, were deposited at the American Type Culture Collection identified as ATCC #20690 on Nov. 17, 1983 by Cetus Corporation. The growth and expression of this plasmid in yeast referred to in the following paper: Innis, M. A., M. J. Holland, P. C. McCabe, G. E. Cole, V. P. Wittman, R. Tal, K. W, K. Watt, D. H. Gelfand, J. P. Holland, and J. H. Meade (1985) Expression, glycosylation, and secretion of an Aspergillus glucoamylase by Saccharomyces cerevisiae. Science 228:21–26.

A method to remove plasmids from yeast for replication in E. coli which we have found works for pGAC9 is given in the following paper: Hoffman, C. S. and F. Winston (1987) A ten-minute DNA preparation from yeast efficiently releases autonomous plasmids for transformation of Escherichia coli. Gene 57:267–272. The pBR322 sequence allows autonomous replication of the plasmid in E. coli and contains the ampicillin gene. The Enol promoter and terminator are two regions from the enolase gene that allow expression of the glucoamylase gene in yeast. The Leu2 sequence allows selection of yeast transformation on leucine-deficient media. The yeast 2μ sequence allows autonomous replication of the plasmid in yeast. PstI, EcoRI, HindIII, BamHI and SalI are restriction endonuclease sites.

The process for the production of glucoamylase from A. niger and A. awamori is set forth by Pazur et al. (18). The Pazur reference discloses in detail the production and isolation of the glucoamylase enzyme which has been further developed by Clarke and Svensson (19) using affinity chromatography on acarbose-Sepharose.

Glucoamylase can be commercially obtained from Novo Nordisk A/S, Bagsvaerd, Denmark; Cultor Ltd., Helsinki, Finland; and Gist-Brocades, Delft, The Netherlands. Pullulanase can be obtained from Novo Nordisk. Isoamylase can be obtained from Sigma Chemical Corp., St. Louis, Mo., U.S.A.

The following experimental evidence exemplifies the selectivity and activity of the subject mutated glucoamylase in accordance with the present inventive process for enzymatically deriving glucose from starch.

EXPERIMENTATION

1. Comparative Kinetic Parameters of Mutated Glucoamylases Measured Using Maltose, Isomaltose and Maltoheptaose as Substrates A comparative study was conducted on 6 mutant glucoamylases expressed in Saccharomyces cerevisiae (10, 20). Comparisons between the kinetic parameters of the six mutated glucoamylases were measured using maltose, isomaltose and maltoheptaose as substrates and compared with those of wild-type glucoamylase. Wild-type glucoamylase refers to the unmutated glucoamylase expressed in Saccharomyces cerevisiae. The experiment was conducted to indicate the selectivity for the enzymes for hydrolysis of $\alpha$-(1→4)-bonds (maltose) as compared to $\alpha$-(1→6)-bonds (isomaltose).

2. Materials and Methods

Enzymes, reagents, and construction of mutations using cassette mutagenesis were carried out as described earlier (10). The Leu177 His and Trp178 Arg mutations were constructed in the SnaBI-HpaI cassette as previously described (11) with 5'-ATAGT-TAACTTCTTCCC AGTGAT-CATATCCTGTCTG-3' and 5'-ATAGT-TAACTTCTTCGCGG-AGAT-CATATCCTGTCTG-3', respectively. The Asn18-2→Ala mutation was constructed in the HpaI-ApaI cassette by using the nucleotides 5'-ATGGGCCCGGTGTTGCACAGCAAT-CGTAAAG-3' and 5'-GCTGGCTCGTCTTTCTTTACGATTGCTCT-3' as cassette and mutagenic primers, respectively, containing a 15-base-pair overlap (21). The following oligonucleotides were used for construction of the 119, 183 and 184 mutants.

Ser ⟶ Tyr119 CGG CCG CCC CCA GTA ACC AGT GTA G

Gly ⟶ Lys183 CGT AAA GAA AGA GCT CTT GTT AAC TTC TTC

Ser ⟶ His184 CGT AAA GAA AGA GTG GCC ATT AAC TTC TTC
CCA

Construction of these mutants were carried out as described above.

Production, purification, and kinetic characterization of the mutated enzymes was performed as set forth in Sierks et al., 1989 (10). Results shown in Table V were obtained on the 119, 183 and 184 mutants where glucoamylase activity was determined as described above, except at 45° C.

3. Results and Discussion

Six mutations, Ser119→Tyr, Leu177→His, Trp178→Arg, and Asn182→Ala, Gly183→Lys, and Ser184→His were constructed in the cloned *A. awamori* glucoamylase gene by cassette mutagenesis and expressed in *S. cerevisiae*.

Results of the kinetic studies of the six mutations using maltose, maltoheptaose, and isomaltose as substrates are given in Tables I and V. The above results produced selectivities for the mutants in positions 119, 183, and 184 set forth in Table VI.

Values of $k_{cat}$ for the Leu177→His mutation also decreased for all three substrates compared to wild-type glucoamylase, that for isomaltose more than tenfold and those for maltose and maltoheptaose fivefold. $K_M$ values increased less than 50% for maltoheptaose and isomaltose but threefold for maltose. Selectivity for isomaltose over maltose hydrolysis was again relatively unchanged from that of wild-type enzyme, while that for maltoheptaose over maltose cleavage doubled. Although replacement of the aliphatic and hydrophobic Leu177 by the aromatic and hydrophilic His hardly affected selectivity of maltose over isomaltose, sequence similarity suggests that a hydrophobic aromatic ring, found at this position in all of the α-amylases except Taka-amylase A, should increase it.

The $k_{cat}$ values for the Trp178→Arg mutation decreased five- to eightfold for the three substrates compared to wild-type glucoamylase. $K_M$ values decreased slightly for maltose and increased slightly for maltoheptaose when compared to the wild-type enzyme. The $K_M$ value for isomaltose, however, more than doubled, leading to a doubling of the selectivity for maltose over isomaltose hydrolysis. Selectivity for maltoheptaose over maltose cleavage was unchanged.

Values of $k_{cat}$ for the Asn182→Ala mutation for each of the three substrates decreased slightly compared to wild-type glucoamylase, but not nearly to the extent of the other mutations. The $K_M$ value for maltose decreased slightly, the value for maltoheptaose increased slightly, and the value for isomaltose doubled. These changes in binding are reflected in a more than doubling of selectivity for maltose over isomaltose cleavage compared to wild-type glucoamylase, as well as in a significant decrease of selectivity for maltoheptaose over maltose hydrolysis.

The Trp178→Arg and Asn182→Ala mutations led to the desired increases in selectivity for maltose over isomaltose hydrolysis, although the former was accompanied by a much greater decrease in values of $k_{cat}$ for the three substrates than the latter. These two mutations were based on substitutions to make the glucoamylase active site more like the active site of amylases, which lack the capability to hydrolyze α-(1→6)-D-glucosidic bonds. Since the binding of maltose and isomaltose was differentially affected by the two mutations, while values of $k_{cat}$ were decreased by the same relative amounts for all three substrates, Trp178 and Asn182 affect subsite 2 in such a way that they interact more strongly with maltose than with isomaltose.

Kinetic parameters of the Ser119→Tyr mutant displayed a slightly higher $k_{cat}$ and lower $K_M$ for maltose and a slightly higher $k_{cat}$ and two-fold higher $K_M$ value for isomaltose. This resulted in an increased specificity by over two-fold for maltose over isomaltose. The Gly183→Lys mutant showed slightly increased $k_{cat}$ and decreased $K_M$ values with maltose and increased $k_{cat}$ and $K_M$ values for isomaltose resulting in a slight increase in selectivity. Finally, the Ser184 His mutant also increased $k_{cat}$ and decreased $K_M$ for maltose, with little effect on the isomaltose kinetic parameters. This produced an increased relative specificity of just under two-fold for this mutant.

The above results show that all of the mutations based on sequence homology (119, 178, 182, 183, and 184) with the α-(1→4) enzymes resulted in increased selectivity for maltose hydrolysis, and all but the 178 mutation had only slightly reduced if not better activity. There is good evidence therefore that other mutations in these two regions as well as in the third region of similarity (Region 6) will also provide an increase in selectivity. This is also evidence that the amino acids selected by applicant may not be the only or even best choices at a particular position, since in a number of cases more than one amino acid could have been picked. This provides significant grounds to conclude that any mutation in these three regions and any amino acid at one of the positions are encompassed within the present invention.

These mutations demonstrate that it is possible to predict functional changes in enzymatic activity based entirely on homology, with enzymes for which no three-dimensional structure is known, but for which functional differences exist that can be correlated with known functional residues.

4. Condensation studies for Asn182→Ala and Wild-Type glucoamylases

At high glucose concentrations, glucoamylases catalyze condensation reactions of which isomaltose is the most significant accumulated product. The following experiment compares the catalyses of the condensation reactions for Asn182→Ala and wild-type glucoamylases.

30% (wt/wt) initial glucose in 0.1 M sodium acetate buffer in deuterium oxide at pH4.5 was incubated at 35° C. Asn182→Ala and wild-type enzyme concentrations were 10 and 5 mg/ml, respectively. The rate of product formation represents the sum of isomaltose and isomaltotriose as monitored by $^1$H NMR spectrometry at 500 MHz measured at 4.94 ppm on a Bruker AM 500 spectrometer.

Figure 4:
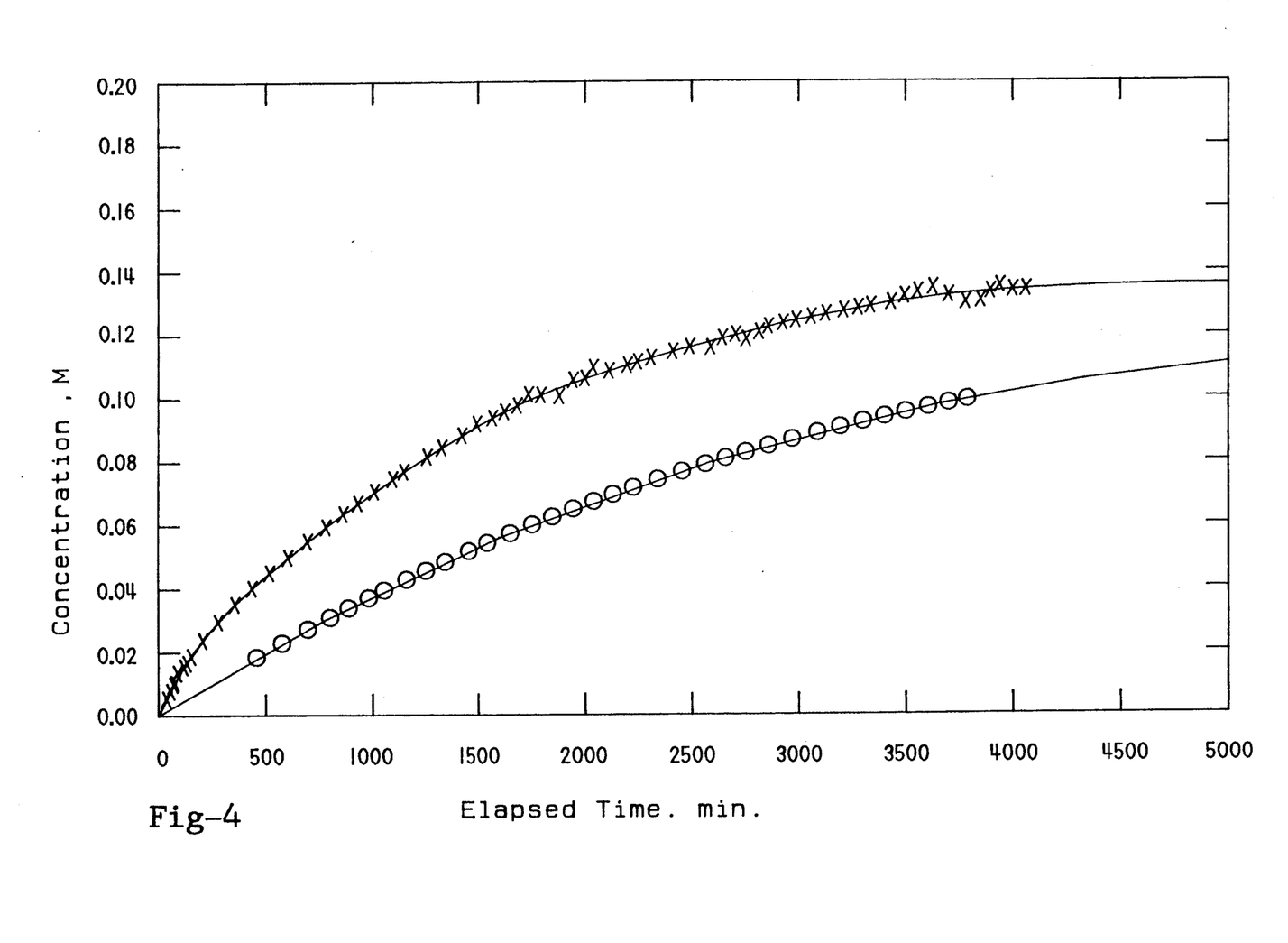
FIG. 4 shows data from condensation reaction studies for Asn182→Ala and wild-type glucoamylases. Conditions for reactions were 30% (wt/wt) initial glucose in 0.1 M sodium acetate buffer in deuterium oxide at pH 4.5 and 35° C. Asn182+Ala and wild-type enzyme concentrations were 10 and 5 mg/ml, respectively. Rate of product formation represents the sum of isomaltose and isomaltotriose as monitored by $^1$H NMR spectrometry (22) at 500 Mhz measured at 4.94 ppm on a Bruker AM-500 spectrometer. o represents Asn182→Ala and + wild-type enzyme. The initial ratio of rates of formation rates of α-(1→6)-to α-(1→4)-bonds for Asn182→Ala is 22% that of wild-type glucoamylase.

In FIG. 4, o represents Asn182→Ala and + wild-type enzyme. When corrected for the differences in enzyme concentrations, the initial ratio of formation rates of α-(1→6)- to α-(1→4)- bonds for Asn182 Ala mutant is 22% that of wild-type glucoamylase as determined by curve fitting (22).

The data shows that the initial rate of isomaltose formation catalyzed by the Asn182→Ala mutant decreased 5-fold compared to wild-type glucoamylase as shown in FIG. 4. This is due to the specific destabilization of the isomaltose transition state complex. This experiment shows a mechanism of action by which the mutant enzyme may raise the glucose yield from concentrated starch solution above the 95% normally obtained.

At sixty hours of incubation the total concentration of isomaltose and isomaltotriose produced by wild-type glucoamylase was approaching its equilibrium value (about 0.14 m), while that produced by twice as much of the Asn182+Ala mutant was less than 0.1M.

5. Comparative Study of Asn182→Ala Mutated Enzyme versus Unmutated Enzyme with Regard to Glucose Yield The following experiments compare glucose yield (glucose concentration, g/L) between native glucoamylase from *Aspergillus niger* with and without debranching enzymes, wild-type glucoamylase from *Sacchromyces cerevisiae* with and without debranching enzymes, and Asn182→Ala glucoamylase from *Sacchromyces cerevisiae* with and without debranching enzymes. As discussed above, the two debranching enzymes used, pullulanase and isoamylase, have already been used to a limited extent for this purpose. Neither debranching enzyme can hydrolyze α-(1→6) bonds in substrates with fewer than about four glucosyl residues. Accordingly, the enzymes cannot hydrolyze isomaltose, which has only two glucosyl residues.

The equilibrium between glucose and isomaltose remains unchanged. This occurs not matter what enzyme is being used. Since the equilibrium is determined solely by the thermodynamics of the reaction, a change in the relative rate at which two molecules of glucose are made by the hydrolysis of isomaltose will be matched by the same proportional change in the rate at which isomaltose is made by the condensation of two molecules of glucose. This is dependent upon microscopic reversibility of the system.

6. Materials and Methods

The strain of *Sacchromyces cerevisiae* yeast carrying the glucoamylase from *Aspergillus awamori*, either mutated (Asp182→Ala) or unmatched (designated as wild-type) are grown at 30° C. for 72 hours in ten liter batches in a 19-liter Lab-Line Bioengineering fermenter in the Iowa State University Fermentation Facility. The growth medium initially contained 2% glucose, 1.7 g/L yeast nitrogen base, 5 g/L ammonium sulfate, 100 mg/L L-histidine, but no leucine. Since the plasmid carrying the glucoamylase gene coded for L-leucine production while the parent yeast strain did not, L-leucine was excluded from the medium. The medium was kept at pH 4.5 by the addition of ammonium hydroxide. Air was added to the medium so that oxygen remained at 80% of saturation. Glucose was added at 27, 52, and 60 hours to bring its concentration back to 2%, or was added only once, at 48 hours, again to 2% so that the effect of glucose concentration on glucoamylase yield could be studied.

The fermentation broth was filtered by an ultrafiltration membrane and the clear supernatant containing the wild-type or mutated glucoamylase was collected. The collected supernatants were concentrated by ultrafiltration to 100 mL, freeze dried, redissolved, dialyzed, and added to a DEAE-Fractogel column, which was eluted by either a decreasing pH gradient or an increasing sodium chloride gradient. The fractions holding the glucoamylase activity were passed to a column of Sepharose coupled acarbose, a pseudo-tetrasaccharide that specifically inhibits glucoamylase. The glucoamylase-acarbose complex was broken by use of 1.7M Tris eluant (19).

Purified glucoamylase samples of the three types were incubated in DE15 dextrin at pH 4.5 and 35° C. for 120 hours. The three types were 1) *A. awamori* glucoamylase obtained from Miles Laboratories, Elkhart, Ind., U.S.A., with the glucoamylase I form (the same as produced by the glucoamylase gene inserted in *S. cerevisiae*) separated by column chromatography and purified virtually to homogeneity, 2) wild-type glucoamylase produced by yeast fermentation, and 3) mutated glucoamylase (Asp182→Ala) produced the same way. Each of the three glucoamylase types was incubated three different ways: either alone at 4.5 IU/mL, at 4.5 IU/mL with 4.5 IU/mL pullulanase and at 4.5 IU/mL with 4.5 units/mL isoamylase. All enzyme activities were measured in international units (IU) except for isoamylase where a unit was defined as an increase of light absorbance at 60 nm of 0.1 in a 10-mm cuvette following hydrolysis of rice starch for one hour and use of a reducing sugar assay. In all nine experiments, glucose concentration was measured after oxidation with glucose oxidase by a spectrophotometric method.

7. Results

The best results were obtained when glucose was allowed to fall to zero concentration near 20 hours and remained there until 48 hours. At 48 hours, enough glucose was added to bring the concentration back to 2%. During the period of glucose starvation, the yeast presumably grew on the organics in the yeast-nitrogen base, as no decrease in growth rate was noted. Glucoamylase production started when glucose reached zero concentration.

Normally, glucoamylase is purified by passage through DEAE-Fractogel column with a decreasing linear gradient of pH 6 to 3. The mutated enzyme, however, was not adsorbed well under these conditions as a large part exited at the void volume. Therefore, it was purified at pH 6 using a linear salt gradient from 0.0 to 0.4M sodium chloride. Only one glucoamylase peak was obtained with this column and with a column packed with acarbose, a potent glucoamylase inhibitor, coupled to Sepharose.

Referring to Tables II-IV, glucose yields were highest when dextrin was hydrolyzed at 35° C. and pH 4.5 with glucoamylase mixed with either pullulanase or isoamylase, which rapidly cleaved α-(1→6) bonds in the substrate molecules, thereby allowing the glucoamylase to hydrolyze the remaining α-(1→4) bonds faster. This behavior has been noted by others, and in fact such mixtures are often used commercially. Mutant glucoamylase gave slightly higher glucose yields than did either native glucoamylase from *A. awamori* or wild-type glucoamylase from yeast, with the differences being statistically significant. Peak glucose concentrations were attained near 60 hours similar to industrial production of glucose with glucoamylase, which however occurs at 60° C. rather than 35° C.

Of significance, comparing Tables II, III and IV, is that the glucoamylase Asn182→Ala mutant alone (without a debranching enzyme) produced a significant increase in the production of glucose by 1% at a single set of reaction conditions over the native or wild-type glucoamylase. Accordingly, utilizing the process in accordance with the present invention can produce a significant increase in the yield of glucose per unit amount of starch hydrolyzed relative to a yield from incubating the starch and/or related oligo- and polysaccharide molecules in the present of the unmutated glucoamylase having Asn at the amino acid 182.

The above data demonstrates that the glucoamylase enzyme having the Asn182→Ala results in increased selectivity of the enzyme for α-(1+4) bonds over α-(1→6) bond formation as well as a 1% increase in glucose production. Commercially, even marginal improvements over the 95% yields of glucose are significant.

Applicant has demonstrated that the addition of pullulanase orisoanylase to glucoamylase always gives a more rapid approach to maximal glucose yield. The addition of pullulanase give a slightly higher maximal yield than does glucoamylase alone, probably because the debranching enzymes rapidly cleave α-(1→6) bonds that impede hydrolysis of α-(1→4) bonds by glucoamylase. The addition of isoamylase was less effective in increasing maximal glucose yield, both results supporting the findings of others in the field.

The Asn182→Ala mutant glucoamylase gave slightly higher maximal yields than did the native or wild-type enzymes, the native and wild-type enzymes presumably being identical to each other except for additional glycosylation in the wild-type enzyme added by the *S. cerevisiae* (20). The mutant enzyme will pullulanase or isoamylase gave a higher yield than did the native or wild-type enzymes with pullulanase or isoamylase.

In conclusion, the above mutant glucoamylase enzymes used in accordance with the present inventive method provide an increased yield of glucose per unit amount of starch hydrolyzed relative to a yield of incubating the starch and/or related oligo- and polysaccharide molecules in the presence of unmutated glucoamylases, thereby providing a commercially valuable inventive process.

Further, experimental evidence demonstrates that comparisons of enzyme primary structure and use of information on functional residues can lead to a prediction of altered formation following amino acid replacement.

TABLE I

Kinetic parameters for hydrolysis of maltose, maltoheptaose, and isomaltose by mutant and wild-type *A. awamori* glucoamylases at pH 4.4 and 50° C.

| | Leu177 → His | Trp178 → Arg | Asn182 → Ala | Wild type |
|---|---|---|---|---|
| Maltose ($G_2$) | | | | |
| $k_{cat}$ (s$^{-1}$) | 2.6 ± 0.1 | 1.86 ± 0.11 | 11.6 ± 0.3 | 14.4 ± 0.5 |
| $K_M$ (mM) | 5.3 ± 0.5 | 1.52 ± 0.28 | 1.38 ± 0.10 | 1.73 ± 0.14 |
| $k_{cat}/K_M$ (mM$^{-1}$s$^{-1}$) | 0.49 | 1.22 | 8.4 | 8.3 |
| Maltoheptaose ($G_7$) | | | | |
| $k_{cat}$ (s$^{-1}$) | 15.9 ± 0.8 | 16.6 ± 0.4 | 65 ± 4 | 84 ± 2 |
| $K_M$ (mM) | 0.30 ± 0.04 | 0.26 ± 0.02 | 0.26 ± 0.04 | 0.22 ± 0.02 |
| $k_{cat}/K_M$ (mM$^{-1}$s$^{-1}$) | 53 | 63 | 250 | 390 |
| Isomaltose (i$G_2$) | | | | |
| $k_{cat}$ (s$^{-1}$) | 0.0438 ± 0.0018 | 0.0728 ± 0.0027 | 0.397 ± 0.019 | 0.487 ± 0.031 |
| $K_M$ (mM) | 49.7 ± 5.7 | 7.31 ± 6.6 | 64.3 ± 6.1 | 36.0 ± 4.7 |
| $k_{cat}/K_M$ (mM$^{-1}$s$^{-1}$) | 0.000881 | 0.000997 | 0.00618 | 0.0135 |
| $\dfrac{k_{cat}/K_M (G_7)}{k_{cat}/K_M (G_2)}$ | 110 | 52 | 30 | 47 |
| $\dfrac{k_{cat}/K_M (G_2)}{k_{cat}/K_M (iG_2)}$ | 550 | 1230 | 1370 | 620 |

TABLE II

Production of glucose from DE15 dextrin by native glucoamylase from *Aspergillus niger* with and without debranching enzymes

| | Glucose concentration, g/L | | |
|---|---|---|---|
| Elapsed time, h | Gluco-amylase | Glucoamylase + Pullulanase | Gluco-amylase + Isoamylase |
| 12 | 172, 182, 190 | 205, 213, 227 | 202, 211, 225 |
| 25 | 215, 231, 233 | 237, 251, 259 | 239, 243, 247 |
| 30 | 236, 241, 252 | 252, 270, 273 | 246, 248, 271 |
| 36 | 245, 260, 278 | 266, 279, 280 | 260, 267, 274 |
| 46 | 263, 277, 282 | 279, 285 | 282, 287 |
| 51.5 | 281, 288 | 285, 295 | 284, 291 |
| 57.5 | 287, 291 | 279, 289, 291, 301 | 286, 290, 297 |
| 61.5 | 277, 285, 290 | 289, 294 | 286, 294 |
| 70.5 | 279, 285, 285, 291 | 283, 287 | 280, 294 |
| 78 | 274, 282, 284 | 280, 285 | 279, 291 |
| 83.5 | 280, 284 | 282, 290 | 285, 291 |
| 96 | 279, 279, 285 | 277, 289 | 279, 287 |
| 104.5 | 279, 282 | 279, 283, 284, 287 | 274, 280, 283, 292 |
| 120 | 274, 280 | 275, 280, 281, 285 | 276, 282 |
| Max. glucose, g/L | 287.7 ± 4.1* | 291.3 ± 4.1* | 290.7 ± 4.5* |
| time max, h | 63.1 | 59.6 | 63.9 |
| Slope after 70 h, g/L·h | −0.123 ± 0.060** | −0.086 ± 0.058** | −0.164 ± 0.099** |

*95% confidence limit.
**Standard error.

TABLE III

Production of glucose from DE15 dextrin by wild-type glucoamylase from *Saccharomyces cerevisiae* with and without debranching enzymes

| | Glucose concentration, g/L | | |
|---|---|---|---|
| Elapsed time, h | Gluco-amylase | Glucoamylase + Pullulanase | Gluco-amylase + Isoamylase |
| 12 | 171, 180 | 190, 196 | 182, 192 |
| 25 | 218, 220 | 231, 245 | 214, 236 |
| 30 | 230, 243 | 241, 249 | 231, 235 |
| 36 | 249, 269 | 243, 257 | 257, 263 |
| 46 | 266, 280 | 264, 286 | 256, 284 |
| 51.5 | 270, 286 | 289, 301 | 270, 289 |
| 57.5 | 267, 303 | 288, 292 | 280, 289, 292 |
| 61.5 | 284, 292 | 288, 290 | 281, 287 |
| 70.5 | 278, 285, 292 | 276, 288, 300 | 279, 290 |
| 78 | 284, 288 | 274, 274, 280 | 281, 285 |
| 83.5 | 272, 278 | 280, 289 | 280, 284, 291 |
| 96 | 280, 286 | 280, 284 | 276, 279, 285 |
| 104.5 | 277, 282 | 283, 284 | 275, 279, 280, 281 |
| 120 | 278, 279, 283 | 278, 281, 284 | 278, 282, 286 |
| Max. glucose, | 288.3 ± 6.1* | 288.6 ± 5.2* | 286.8 ± 6.0* |

TABLE III-continued

Production of glucose from DE15 dextrin by wild-type glucoamylase from *Saccharomyces cerevisiae* with and without debranching enzymes

| | Glucose concentration, g/L | | |
|---|---|---|---|
| Elapsed time, h | Glucoamylase | Glucoamylase + Pullulanase | Glucoamylase + Isoamylase |
| g/L time max.[h] | 66.4 | 62.5 | 67.3 |
| Slope after 70 h, g/L·h | −0.088 ± 0.075** | −0.046 ± 0.098** | −0.088 ± 0.066** |

*95% confidence limit.
**Standard error.

TABLE IV

Production of glucose from DE15 dextrin by wild Asn182→Ala glucoamylase from *Saccharomyces cerevisiae* with and without debranching enzymes

| | Glucose concentration, g/L | | |
|---|---|---|---|
| Elapsed time, h | Glucoamylase | Glucoamylase + Pullulanase | Glucoamylase + Isoamylase |
| 12 | 189, 194 | 229*, 235* | 201, 241* |
| 25 | 229, 247 | 237, 247 | 233, 235 |
| 30 | 247, 252 | 252, 262 | 257, 269 |
| 36 | 258, 276 | 280, 286 | 259, 280 |
| 46 | 261*, 266* | 271*, 310* | 286, 293 |
| 51.5 | 288, 292 | 289, 299 | 286, 293 |
| 57.5 | 289, 294 | 291, 299 | 287, 292 |
| 61.5 | 280, 289 | 279, 285, 289, 295 | 280, 286 |
| 70.5 | 280, 288 | 281, 287 | 275, 289 |
| 78 | 281, 287 | 277, 289 | 283, 290 |
| 83.5 | 283, 287 | 276, 288 | 279, 286 |
| 96 | 279, 284 | 279, 284 | 276, 284, 285, 287 |
| 104.5 | 282, 284 | 273, 285, 291 | 284, 286 |
| 120 | 276, 280, 284 | 279, 285, 291 | 279, 283 |
| Max. glucose, g/L | 290.7 ± 4.3** | 293.0 ± 5.7** | 291.2 ± 5.4** |
| time max.[h] | 61.6 | 58.5 | 60.6 |
| Slope after 70 h, g/L·h | −0.088 ± 0.051*** | −0.029 ± 0.093*** | −0.033 ± 0.081*** |

*Not used in nonlinear regression.
**95% confidence limit.
***Standard error.

TABLE V

Kinetic constants for mutants determined at 45 C., pH 4.5, using a 0.05M sodium acetate buffer. Values for $k_{cat}$ are in s$^{-1}$, and $K_M$ are in mM.

| | Maltose | | | Maltoheptaose | | | Isomaltose | | |
|---|---|---|---|---|---|---|---|---|---|
| Enzyme | $k_{cat}$ | $K_M$ | $k_{cat}/K_M$ | $k_{cat}$ | $K_M$ | $k_{cat}/K_M$ | $k_{cat}$ | $K_M$ | $k_{cat}/K_M$ |
| Wild-type | 9.1 | 1.4 | 6.4 | 66.2 | 0.14 | 472.9 | 0.34 | 30.3 | 1.13 E-2 |
| Ser→Tyr119 | 10.1 | 1.1 | 9.6 | 77.9 | 0.20 | 389.4 | 0.48 | 66.2 | 7.25 E-3 |
| Gly→Lys183 | 10.4 | 1.1 | 9.6 | 72.0 | 0.14 | 514.2 | 0.53 | 39.0 | 1.36 E-2 |
| Ser→His184 | 9.8 | 0.9 | 10.9 | 79.3 | 0.14 | 566.6 | 0.29 | 26.7 | 1.10 E-2 |

TABLE VI

Selectivities of mutant enzymes for maltose (G2) over isomaltose (iG2) and maltoheptaose (G7) over maltose.

| | WT | S→Y119 | G→K183 | S→H184 |
|---|---|---|---|---|
| G2/iG2 | 564 | 1320 | 709 | 995 |
| G7/G2 | 74 | 41 | 53 | 52 |

What is claimed is:

1. A process for converting starch or partially hydrolyzed starch into a syrup containing dextrose, said process including the steps of: increasing the selectivity of the glucoamylase or related enzyme for α-(1→4) glucosidic bonds by the glucoamylase or related enzyme by introducing into the mutated enzyme at least one mutation substituting an amino acid of the glucoamylase or related enzyme with at least one amino acid wherein the amino acid position corresponding to Ser119 of glucoamylase from *Aspergillus niger* or related enzymes is mutated to Tyr, the amino acid position corresponding to Asn182 in glucoamylase from *Aspergillus niger* or related enzymes is mutated to Ala, the amino acid position corresponding to Ser184 of glucoamylase from *Aspergillus niger* or related enzymes is mutated to His, and the amino acid position corresponding to Gly183 in glucoamylase from *Aspergillus niger* or related enzymes is mutated to Lys, and saccharifying starch hydrolyzate in the presence of the mutated glucoamylase or related enzyme.

2. A process for converting starch or partially hydrolyzed starch into a syrup containing dextrose, said process including the steps of: increasing the selectivity of the glucoamylase or related enzyme for α-(1→4) glucosidic bonds by the glucoamylase or related enzyme by introducing into the mutated enzyme at least one mutation substituting an amino acid of the glucoamylase or related enzyme with at least one amino acid chosen from the structurally similar regions of other enzymes that selectively hydrolyze only α-(1→4)-glucosidic bonds, said step of increasing the selectivity being further defined as introducing no more than one mutation at an amino acid position in each of a substrate binding region corresponding to *A. niger* Region 1 residues 109-122, Region 4 residues 172-184, and Region 6 residues 382-398 mutated to amino acids chosen by comparison with the structurally similar regions of other enzymes that selectively hydrolyze only α-(1→4)-glucosidic bonds and saccharifying starch hydrolyzate in the presence of the mutated glucoamylase or related enzyme.

3. A process as set forth in claim 1, wherein the glucoamylase is derived from a strain of a filamentous fungus.

4. A process as set forth in claim 3, wherein the glucoamylase is derived from *Aspergillus*.

5. A process as set forth in claim 10 wherein the glucoamylase is derived from *A. niger* or *A. awamori*.

6. A process as set forth in claim 1, wherein the dosage of glucoamylase is in the range from 0.05 to 0.5 AG units per gram of dry solids.

7. A process as set forth in claim 1, comprising saccharification of a starch hydrolyzate of at least 30 percent by weight of dry solids.

8. A process as set forth in claim 1, wherein the saccharification is conducted in the presence of a debranching enzyme selected from the group of pullulanase and isoamylase.

9. A process as set forth in claim 8, wherein the debranching enzyme is a pullulanase derived from *Bacillus*

*acidopullulyticus* or an isoamylase derived from *Pseudomonas amyloderamosa*.

10. A process as set forth in claim 1, wherein the saccharification is conducted at a pH of 3 to 5.5 and at a temperature of 30° to 60° C. for 48 to 72 hours.

11. A process as set forth in claim 10, wherein the pH is from 4 to 4.5 and the temperature is from 55° to 60° C.

12. A method of increasing selective for hydrolysis of an α-(1-4)-glucosidic bond in a mutein derived from a glucoamylase or from an enzyme functionally similar to glucoamylase in its native capability to hydrolyze both α-(1→4) and α-(1→6)-glucosidic bonds, wherein site-specific mutagen is used to substitute an amino acid in the native amino acid sequence of a glucoamylase, or functionally similar enzyme, at one or more amino acid positions selected from the group consisting of amino acid positions corresponding to the *A. niger* glucoamylase Region 1, positions 109-122, and the *A. niger* glucoamylase Region 4, positions 172-184, and the *A. niger* glucoamylase Region 6, positions 382, 398, and wherein the amino acid substituted in the mutein is chosen by comparison with the amino acid residues present in the structurally similar regions of other enzymes that selectively hydrolyze α-(1→4) glucosidic bonds.

* * * * *